United States Patent [19]
Yoon

[11] Patent Number: 5,429,609
[45] Date of Patent: Jul. 4, 1995

[54] ENDOSCOPIC PORTAL FOR USE IN ENDOSCOPIC PROCEDURES AND METHODS THEREFOR

[76] Inventor: InBae Yoon, 2101 Highland Ridge Dr., Phoenix, Md. 21131

[21] Appl. No.: 220,359

[22] Filed: Mar. 31, 1994

Related U.S. Application Data

[63] Continuation-in-part of Ser. No. 40,560, Mar. 31, 1993, Pat. No. 5,389,080, which is a continuation-in-part of Ser. No. 557,869, Jul. 26, 1990, Pat. No. 5,395,342.

[51] Int. Cl.[6] .......................................... A61M 39/04
[52] U.S. Cl. ....................................... 604/167; 604/256
[58] Field of Search ................................ 604/167, 256

[56] References Cited

U.S. PATENT DOCUMENTS

| | | |
|---|---|---|
| 3,044,461 | 7/1962 | Murdock . |
| 3,509,883 | 5/1970 | Dibelius . |
| 3,747,812 | 7/1973 | Karman et al. . |
| 3,788,318 | 1/1974 | Kim et al. . |
| 3,789,852 | 2/1974 | Kim et al. . |
| 3,833,003 | 9/1974 | Taricco . |
| 3,895,632 | 7/1975 | Plowiecki . |
| 3,994,287 | 11/1976 | Turp et al. . |
| 4,177,814 | 12/1979 | Knepshield et al. . |
| 4,187,849 | 2/1980 | Stim . |
| 4,240,411 | 12/1980 | Hosono . |
| 4,379,458 | 4/1983 | Bauer et al. . |
| 4,475,548 | 10/1984 | Muto . |
| 4,524,770 | 6/1985 | Orandi . |
| 4,535,773 | 8/1985 | Yoon . |
| 4,601,710 | 7/1986 | Moll . |
| 4,654,030 | 3/1987 | Moll et al. . |
| 4,655,752 | 4/1987 | Honkanen et al. . |
| 4,668,221 | 5/1987 | Luther . |
| 4,735,614 | 4/1988 | Yapp et al. . |
| 4,769,005 | 9/1988 | Ginsburg et al. . |
| 4,790,817 | 12/1988 | Luther . |
| 4,808,168 | 2/1989 | Warring . |
| 4,899,729 | 2/1990 | Gill et al. . |
| 4,902,280 | 2/1990 | Lander . |
| 4,919,653 | 4/1990 | Martinez et al. . |
| 4,931,042 | 6/1990 | Holmes et al. . |
| 4,943,280 | 7/1990 | Lander . |
| 5,002,557 | 3/1991 | Hasson . |
| 5,030,206 | 7/1991 | Lander . |
| 5,053,016 | 10/1991 | Lander . |
| 5,066,288 | 11/1991 | Deniega et al. . |
| 5,104,383 | 4/1992 | Shichman . |
| 5,104,389 | 4/1992 | Deem et al. . |
| 5,112,321 | 5/1992 | Hiltebrandt . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,129,885 | 7/1992 | Green et al. . |
| 5,139,511 | 8/1992 | Gill et al. . |
| 5,141,498 | 8/1992 | Christian . |
| 5,158,553 | 10/1992 | Berry et al. . |
| 5,161,773 | 11/1992 | Tower ................... 604/167 |
| 5,167,636 | 12/1992 | Clement . |
| 5,176,648 | 1/1993 | Holmes et al. . |
| 5,176,651 | 1/1993 | Allgood et al. . |
| 5,176,697 | 1/1993 | Hasson et al. . |
| 5,180,373 | 1/1993 | Green et al. . |
| 5,183,464 | 2/1993 | Dubrul et al. . |
| 5,188,607 | 2/1993 | Wu ....................... 604/167 |
| 5,197,955 | 3/1993 | Stephens et al. ......... 604/167 |
| 5,201,714 | 4/1993 | Gentelia et al. . |
| 5,207,656 | 5/1993 | Kranys .................. 604/167 |
| 5,209,736 | 5/1993 | Stephens et al. . |
| 5,211,633 | 5/1993 | Stouder, Jr. . |
| 5,234,410 | 8/1993 | Graham et al. .......... 604/167 |
| 5,256,150 | 10/1993 | Quiachon et al. . |

*Primary Examiner*—Paul J. Hirsch

[57] ABSTRACT

An endoscopic portal includes a portal sleeve for insertion through a cavity wall and a valve assembly coupled with the portal sleeve including a bladder having a valve passage therethrough for introduction of instruments of various sizes into the cavity, the bladder having walls forming the valve passage and being normally closed while permitting the valve passage to open to receive the instruments. The bladder is movable by contact with the instruments to move along with the instruments to maintain sealing contact of the bladder with the instruments.

9 Claims, 6 Drawing Sheets

ENDOSCOPIC PORTAL FOR USE IN ENDOSCOPIC PROCEDURES AND METHODS THEREFOR

This application is a continuation-in-part of patent application Ser. No. 08/040,560 filed Mar. 31, 1993, U.S. Pat. No. 5,389,080, which is a continuation-in-part of patent application Ser. No. 07/557,869 filed Jul. 26, 1990, U.S. Pat. No. 5,395,342 the specifications of which are incorporated herein by reference.

BACKGROUND OF THE INVENTION

1. Field of the Invention

The present invention pertains to instruments and methods for use in endoscopic procedures and, more particularly, to an endoscopic portal providing a variable size passage to an operative site within an anatomical cavity to prevent undesired fluid flow through the portal while allowing surgical instruments of various sizes to be selectively introduced through the portal and to methods therefor.

2. Description of the Prior Art

Surgical procedures involving the placement of an endoscopic portal, such as a sleeve or cannula, through a wall of an anatomical cavity to provide a passage for insertion of instruments into the cavity frequently require that the passage be sealed to prevent undesired flow of fluids through the endoscopic portal. For example, in many endoscopic medical procedures access to the interior of an anatomical cavity is gained by utilizing a penetrating instrument, such as a trocar, obturator or needle, having a sharp penetrating point for penetrating a wall of the cavity to establish communication with the interior thereof. Upon penetration of the cavity wall by the penetrating instrument, a sleeve or cannula is left in place for utilization as a portal to introduce instruments into the anatomical cavity. The penetrating instrument is usually received within the sleeve, which passes through the wall of the anatomical cavity with the penetrating instrument and remains in situ after withdrawal of the penetrating instrument therefrom to provide a lumen establishing communication with an operative site in the cavity. The sleeve typically has a proximal end disposed externally of the anatomical cavity and secured in a housing provided with a valve that allows the penetrating instrument to be inserted into and removed from the sleeve. Once the penetrating instrument has been removed from the sleeve, various instruments can be introduced in the anatomical cavity via the lumen of the sleeve dependent upon the operative procedure to be performed.

It is extremely important in endoscopic procedures to prevent undesired fluid flow to and from thee surgical site; and, accordingly, the portal must be sealed prior to and subsequent to the introduction of instruments and while such instruments are in place. In addition, fluids, such as gaseous phase carbon dioxide or nitrous oxide, may be introduced in the anatomical cavity for insufflation as part of the endoscopic procedure, and the escape of such fluids must be prevented during penetration of the cavity as well as during the operative procedure.

The valves of endoscopic portals typically have a valve passage with a size corresponding to an outer diameter or size of the penetrating instrument to form a seal with the penetrating instrument, the size of the penetrating instrument varying in accordance with the endoscopic procedure being performed and the type of anatomical cavity being penetrated. Furthermore, the valves of endoscopic portals typically are designed to close when the penetrating instrument is removed to prevent fluid flow through the valves. Many prior art endoscopic portals utilize a flapper or gate valve that is normally biased to a closed position and movable to an open position to allow the penetrating instrument to be inserted through the valve passage, which has a single, predetermined size corresponding to the size of the penetrating instrument. However, additional instruments to be introduced into the anatomical cavity through the valve passage may be of diverse types and sizes, and it will be appreciated that fluid can escape past smaller size instruments.

Accordingly, many prior art endoscopic portals suffer from the disadvantages of allowing the passage or leakage of fluids when instruments smaller in size than the size of the single valve passage are introduced therethrough or of limiting the instruments to be introduced through the portal to a single size. Many attempts have been made to variably seal endoscopic portals to allow the introduction of various sized instruments therethrough; however, there still exists a great need for an endoscopic portal having a universal valve to prevent the escape of fluid from an anatomical cavity by sealing variably Sized instruments passing through the portal without requiring placement in the portal of seals of various sizes.

SUMMARY OF THE INVENTION

Accordingly, it is a primary object of the present invention to overcome the above described disadvantages of prior art endoscopic portals.

Another object of the present invention is to provide a valve assembly for an endoscopic portal having a compressible valve passage for sealingly contacting instruments of various sizes inserted therethrough, the valve assembly being made in a fashion to cause inversion of the valve passage in response to the instruments being inserted along the valve passage to facilitate insertion of the instruments in the endoscopic portal.

A further object of the present invention is to provide a valve assembly for an endoscopic portal, the valve assembly being pressurized to sealingly engage instruments of various sizes inserted therethrough and having a wall forming a valve passage movable along with instruments inserted through the valve assembly.

An additional object of the present invention is to provide a valve assembly for an endoscopic portal formed as a bladder containing a compressible material and defining a valve passage, the bladder being movable by contact with instruments of various sizes in response to movement of the instruments along the valve passage to facilitate movement of the instruments along the valve passage without tearing of the bladder and while maintaining sealing contact between the bladder and the instruments.

Yet a further object of the present invention is to provide a method of inserting instruments through an endoscopic portal in endoscopic procedures including the steps of inserting an instrument in a valve passage of a bladder of a valve assembly of the endoscopic portal and moving the walls of the bladder forming the valve passage in response to movement of the instrument to seal the instrument in the endoscopic portal.

Some of the advantages of the present invention over the prior art are that various endoscopic procedures can be performed with a single portal thusly reducing instrument cost and the time required to complete endoscopic procedures, a single endoscopic portal can be used with various sizes and types of instruments without requiring manipulation of the endoscopic portal or the addition or interchanging of different sized seals, insertion of instruments of various sizes in the valve assembly is facilitated, tearing of the valve assembly bladder is avoided while maintaining a compressive or sealing force or contact between the bladder and instruments inserted in the valve passage, the valve assembly can be of simplified construction, and the endoscopic portal can be inexpensively manufactured to be economically disposable for single patient use.

The present invention is generally characterized in an endoscopic portal for establishing communication with an anatomical cavity through a wall of the cavity including an elongate tubular sleeve having an open distal end for positioning in the cavity and an open proximal end for positioning externally of the cavity with the sleeve extending through the cavity wall and a valve assembly disposed adjacent the sleeve proximal end for preventing undesired passage of fluid through the sleeve and for forming a seal with instruments of various sizes inserted in the sleeve via the valve assembly. The valve assembly includes a bladder defining a valve passage therethrough for permitting instruments of various sizes to be inserted in and removed from the lumen of the sleeve via the valve passage. The bladder contains a material which, in combination with the bladder walls, causes the valve passage to be normally closed or sealed and allows the valve passage to be opened by instruments inserted in the valve passage. The bladder is fashioned to roll or invert in response to the instruments being moved along the valve passage to facilitate movement of the instruments along the valve passage without tearing, snagging or catching while maintaining sealing contact with the instruments. A method of inserting instruments through an endoscopic portal according to the present invention includes the steps of inserting an instrument through a valve passage in a bladder of a valve assembly of the endoscopic portal and moving the walls of the bladder forming the valve passage in response to movement of the instrument through the valve assembly.

Other objects and advantages of the present invention will become apparent from the following description of the preferred embodiment taken in conjunction with the accompanying drawings wherein identical reference numbers indicate identical parts or parts providing identical functions.

DESCRIPTION OF THE PREFERRED EMBODIMENT

Figure 1:
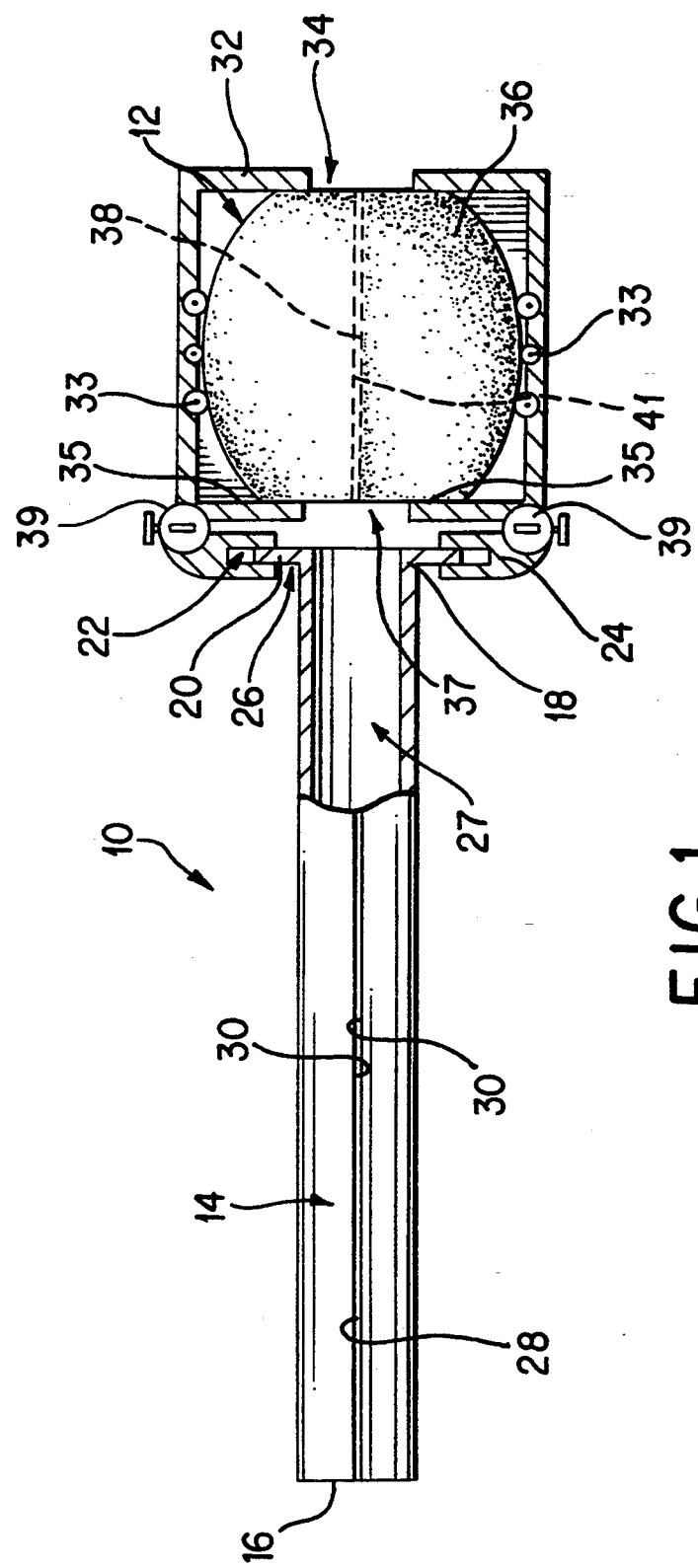
FIG. 1 is a side view, partly in section, of an endoscopic portal according to the present invention.

An endoscopic portal 10 including a valve assembly 12 according to the present invention is illustrated in FIG. 1. Endoscopic portal 10 includes an elongate tubular or cylindrical portal sleeve or cannula 14 for being positioned through a wall of an anatomical cavity during puncture or penetration of the cavity wall by a penetrating instrument to provide access to an operative site within the cavity. Sleeve 14 has an open distal end 16 for being disposed within the anatomical cavity and an open proximal end 18 for being disposed externally of the cavity with the sleeve 14 extending through the cavity wall. Distal end 16 preferably has a blunt configuration to prevent damage to tissue and organ structure within the anatomical cavity and can be non-tapered as shown in FIG. 1 or tapered, such as conically tapered. Sleeve 14 terminates proximally at a flange 20 at proximal end 18, the flange 20 being received in a recess 22 in a forward wall 24 of a housing 25 mounting the proximal end 18 of sleeve 14.

Flange 20 and recess 22 can have various configurations including annular configurations as shown in FIG. 1 with the flange 20 having an outer diameter or size smaller than the outer diameter or size of recess 22 to permit diametric or lateral outward expansion of sleeve 14 as will be explained further below. In addition to the flange 20 and recess 22 shown, sleeve 14 can be permanently or removably coupled to housing 25 in many various ways while allowing or not allowing diametric or outward expansion of sleeve 14. Forward wall 24 has an annular aperture 26 therein allowing passage therethrough by sleeve 14, and the aperture 26 has a diameter or size larger than the outer diameter or size of sleeve 14 to permit diametric expansion thereof.

It will be appreciated that flange 20, recess 22 and aperture 26 can have various configurations with the peripheries of flange 20 and sleeve 14 being disposed within the peripheries of recess 22 and aperture 26, respectively, to permit expansion of sleeve 14. It will be further appreciated that the sizes of flange 20, recess 22 and aperture 26 can be varied in accordance with the amount of expansion desired for sleeve 14 and that, by increasing the gaps or spaces between the periphery of flange 20 and the periphery of recess 22 and between the periphery of sleeve 14 and the periphery of aperture 26, greater expansion of sleeve 14 can be obtained. Where it is desired to limit or control the amount of expansion for sleeve 14, flange 20, recess 22 and aperture 26 can be sized such that the peripheries of flange 20 and/or sleeve 14 contacting the material of forward wall 24 serves as a positive stop or abutment limiting diametric expansion of sleeve 14. It will be further appreciated that where diametric or lateral expansion of sleeve 14 is not desired, no gaps or spaces are needed between flange 20 and sleeve 14, respectively, and the housing forward wall 24.

Sleeve 14 can be made of a suitable rigid, semi-rigid, flexible or bendable medical grade material such as metal or plastic or a flexible, expandable or stretchable material such as rubber permitting sleeve 14 to be normally disposed in a closed, non-flexed, non-expanded or non-stretched state illustrated in FIG. 1 and to be diametrically or laterally expanded or moved in a direction transverse to a longitudinal axis of the sleeve 14 to an open, flexed, expanded or stretched state to increase the diameter or cross-sectional size of the lumen 27 of the sleeve 14 to accommodate instruments or objects therein larger than the diameter or cross-sectional size of the lumen 227 in the closed state. Depending on the material utilized for sleeve 14, a longitudinal slit 28 can be provided through the thickness of the wall of sleeve 14 to extend the entire length thereof to facilitate flexing, expansion or stretching of the sleeve 14. Slit 28 defines opposing edges 30 that touch or are adjacent or Substantially adjacent one another in the closed state and are disposed further apart from one another in the open state. It will be appreciated that sleeve 14 can be made of a rigid material without slit 28 where diametric expansion of sleeve 14 is not desired.

Housing 25 can be made of any suitable material, such as plastic, and can have various configurations including a cylindrical configuration as illustrated in FIG. 1 with an enlarged forward end to facilitate grasping by a surgeon. Preferably, at least the inner surfaces of housing 25 are made of a smooth, slippery material to promote movement of valve assembly 12 as explained further below. Alternatively or in addition to the housing inner surfaces being slippery, the walls of housing 25 can have rollers 33 along the inner surfaces thereof to facilitate movement of the valve assembly 12. Housing 25 has a rear wall 32 with an opening 34 therein longitudinally aligned with the lumen 27 of sleeve 14 to allow various instruments to be inserted through portal 10 via the housing 25. Opening 34 has a diameter or peripheral size larger than the diameter of the lumen 27 to accommodate instruments or objects larger in size than the lumen diameter in the closed state. Housing 25 has internal walls or shoulders 35 spaced proximally from forward wall 24 for confining valve assembly 12 between the shoulders 35 and the housing rear wall 32. Shoulders 35 extend inwardly from the upper and lower walls of housing 25, and the shoulders 35 can extend parallel with forward wall 24 as shown in FIG. 1 or non-parallel. The distance that shoulders 35 extend inwardly from the housing upper and lower walls is sufficient to confine valve assembly 12 and to prevent longitudinal movement thereof when instruments are inserted therethrough as described further below. Preferably, shoulders 35 extend inwardly from the housing upper and lower walls to terminate at an opening 37 that is larger in size than lumen 27 to allow instruments or objects larger than the lumen 27 to be passed through the housing 25. If desired, shoulders 35 can be angled proximally or provided with flanges angled proximally therefrom to enhance inversion or rolling movement of valve assembly 12 when instruments of various sizes are inserted therein as explained further below. Depending on the configuration of housing 25, bladder 36 can be confined in housing 25 in many various ways such as between the front wall and a rear wall or shoulder of the housing. Valves 39 such as stopcocks communicating with the interior of housing 25 can be provided for supplying fluids to the anatomical cavity or for aspirating fluids from the anatomical cavity via lumen 27. The valves 39 can be mounted on housing 25 in many various ways, such as between forward wall 24 and shoulders 35 to facilitate operation by the hand of the surgeon grasping housing 25 as shown in FIG. 1.

Valve assembly 12 includes a bladder 36 disposed in housing 25, the bladder 36 defining a longitudinal valve passage 38 therethrough aligned with lumen 27 and openings 34 and 37. Bladder 36 can be made of any suitable expandable material to form an envelope for holding a material in the interior thereof and to promote movement of bladder 36 when instruments of various sizes are moved along valve passage 38. The bladder 36 can be made of an expandable, medical grade membrane, such as Tecoflex EG-85A manufactured by Thermedics, Inc., Tefilon, Goretex or rubber, allowing instruments or objects to pass easily therethrough. However, the bladder does not have to be made of a tear resistant material and can be made in its entirety of less expensive materials for simplicity and cost reduction.

Figure 3:
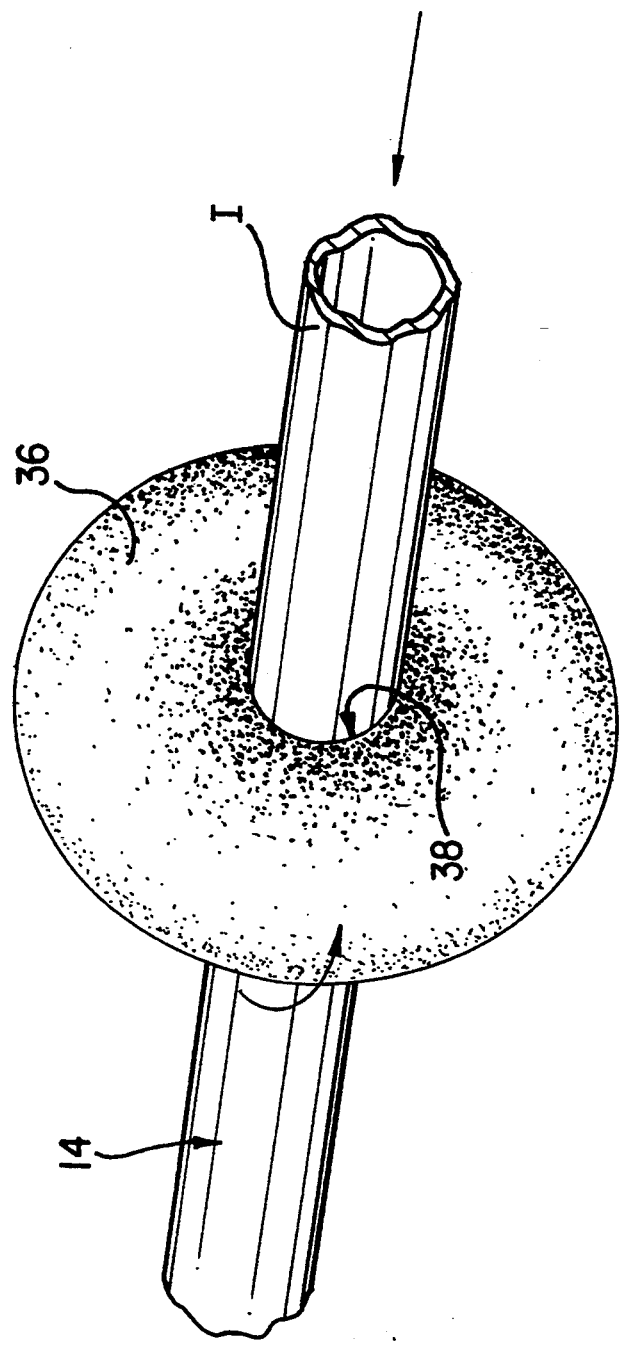
FIG. 3 is a broken perspective view of the valve assembly of FIG. 2 with an instrument extending therethrough.

Bladder 36 contains a material, such as a compressible fluid or solid material including air, water, saline, gel or foam, for example, and has a size and configuration normally closing, collapsing, sealing or compressing the walls of the bladder forming valve passage 38 while allowing the valve passage to open in response to pressure or force applied externally to the bladder 36 by instruments inserted in the valve passage 38. Accordingly, due to the material forming the bladder and/or the compressible material within the bladder, the shape, size and configuration of the bladder normally closes or seals valve passage 38 while allowing temporary deformation or contraction of the bladder 36 to open passage 38 in response to external pressure applied to the bladder 36. Bladder 36 is fashioned to move or invert in response to contact of the walls forming the valve passage with instruments moved through the valve passage 38. Bladder 36 can be fashioned in many ways to move with instruments inserted through the valve passage and to roll, rotate or invert in response to passage of instruments along the valve passage 38; for example, elastic materials and/or a bias can be used in bladder 36 to promote such movement. Bladder 36 is confined against longitudinal movement or displacement by the shoulders 35 and the housing rear wall 32; and, with the bladder 36 disposed in housing 25, the open proximal end 18 of sleeve 14 remains unsealed allowing fluid, such as insufflation gas, to be supplied to the anatomical cavity through the lumen 27. The bladder 36 can be sized and shaped to have various predetermined sizes and configurations, including spherical, partial spherical, heart-shaped, toroidal or donut-shaped, disk-shaped, funnel-shaped, conical or nipple-shaped configurations, the bladder 36 having a toroidal configuration in FIG. 3.

Figure 2:
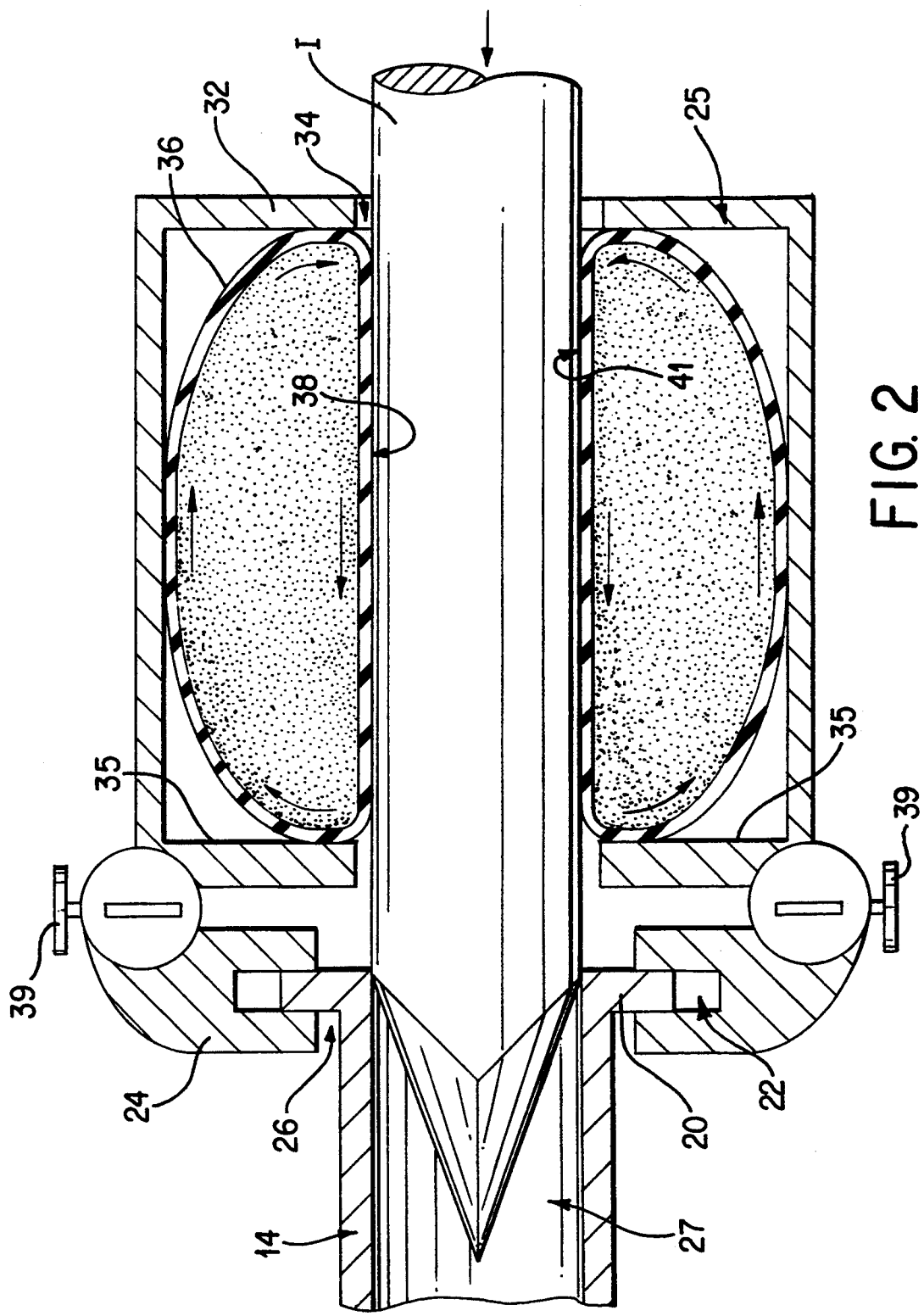
FIG. 2 is an enlarged, broken sectional view of the endoscopic portal of FIG. 1 showing the valve assembly therefor.

According to a method of operation for the endoscopic portal 10 and valve assembly 12 according to the present invention, bladder 36 is filled by the compressible material such that the bladder walls forming valve passage 38 are normally closed or collapsed in a direction transverse to a longitudinal axis of the valve passage 38 to form a seal along the length of the valve passage 38 preventing fluid flow through the valve assembly 12 as shown in FIG. 1, it being noted that valve passage 38 in FIG. 1 is illustrated as being slightly open for the sake of clarity in identifying the valve passage. Bladder 36 is confined in a longitudinal direction between shoulders 35 and housing rear wall 32. Opening 34 in housing rear wall 32 is covered by bladder 36 to form a seal at the housing rear opening 34. Proximal end 18 of sleeve 14 remains uncovered by the bladder 36 to allow fluid to be supplied to or withdrawn from an anatomical cavity via valves 39. An instrument I, such as a penetrating instrument including a trocar, obturator or needle having a sharp tip for penetrating a wall of an anatomical cavity, is inserted through the valve passage 38 to be received within sleeve 14 as described in applicant's copending patent application Ser. No. 07/557,869 filed Jul. 26, 1990, the specification of which is incorporated herein by reference. As shown in FIG. 2 and in FIG. 3, wherein housing 25 is not shown, insertion of the instrument I in valve passage 38 applies external pressure to bladder 36 temporarily deforming the bladder 36 to open valve passage 38 to receive the instrument I. The instrument I is moved forwardly or distally along the valve passage 38 and into sleeve 14 while being sealingly contacted by bladder 36 with a compressive sealing force along valve passage 38, the longitudinal direction of insertion or movement of instrument I being indicated by arrows in FIGS. 2 and 3. Movement of instrument I along the valve passage 38 in the direction of insertion causes movement of bladder 36 with the instrument causing continuous rolling, rotational or inverting movement of bladder 36 as indicated by the arrows in FIGS. 2 and 3 due to the sealing grip of bladder 36 with the instrument I. Movement of the instrument I in the direction of insertion causes the passage-defining portion or walls 41 of the bladder 36 to be moved distally or forwardly causing the valve passage 38 to invert at a forward or distal end thereof and causing the bladder 36 to roll or rotate to accommodate movement of the instrument through the valve assembly. Movement of walls 41 in the direction of insertion causes the walls 43 of bladder 36 opposite the walls 41 to move in a direction opposite the direction of movement of walls 41 as shown by the arrows in FIG. 2. Movement of bladder 36 with instrument I facilitates insertion and passage of instrument I through valve assembly 12 without tearing, snagging or catching of the bladder 36 while allowing the bladder to maintain a compressive seal with the instrument I. With the instrument I extending through valve passage 38, bladder 36 conforms to the size and configuration of the instrument I along the valve passage 38 to be in sealing relation or contact with the instrument I and form a seal along the length of the passage 38 preventing the flow of fluid through valve assembly 12.

Where the instrument I is a penetrating instrument as shown, the instrument I can be utilized to penetrate a wall of an anatomical cavity with the sharp tip protruding beyond the sleeve distal end 16 such that the sleeve 14 passes through the cavity wall during penetration to position distal end 16 within the anatomical cavity while proximal end 18 remains externally of the cavity. During penetration and while the penetrating instrument I is in place, fluid flow to and from the cavity through valve assembly 12 is prevented due to the seal formed by bladder 36 with the penetrating instrument I. Where valves 39 are provided, fluid can be supplied to the anatomical cavity, and such fluid cannot escape through valve assembly 12. Once distal end 16 of sleeve 14 is within the anatomical cavity, the penetrating instrument I can be withdrawn from the endoscopic portal 10 leaving the endoscopic portal 10 in place. It will be appreciated that withdrawal of instrument I through the valve assembly 12 in a direction opposite the direction of insertion will cause bladder 36 to rotate and a rearward end of valve passage 38 to invert in a direction opposite the direction of withdrawal of instrument I. Upon withdrawal of the penetrating instrument I, bladder 36 returns to its initial configuration or state to cause valve passage 38 to automatically close and thusly seal endoscopic portal 10. Instruments of various sizes can be inserted in the anatomical cavity through the lumen 27 of the endoscopic portal 10 with bladder 36 deforming or contracting in response to external pressure applied by the instruments to open valve passage 38 to a size and shape to receive the instruments with bladder 36 forming a seal therewith.

It will be appreciated that various sizes of instruments can be introduced at an anatomical cavity via the endoscopic portal 10 in that the single valve passage 38 will open to a size just large enough to receive the instruments with bladder 36 forming a seal therewith. Instruments larger in size than the diameter of lumen 27 can be introduced into the anatomical cavity and tissue and other objects can be removed from the anatomical cavity in that sleeve 14 can be expanded diametrically or laterally outwardly by the instruments or objects from the closed state wherein edges 30 touch or are separated from one another by a minimal gap to the open state wherein the edges 30 are separated from one another or the gap is increased to expand lumen 27 to a size large enough to receive the instruments or objects.

The bladder is shown confined within the housing; however, the bladder can be extended distally to elongate the valve passage and create a longer seal and more support for instruments passing therethrough. To this end, the bladder can have a nipple-like portion extending partially or entirely through the portal sleeve. By designing the bladder such that the walls move along with the instrument, tearing or other damage to the valve assembly is minimized while permitting the use of elastic or other conformable flexible materials to provide a valve capable of sealing engagement with instruments of varying diameters since there is minimal resistance to passage of the instruments.

Figure 4:
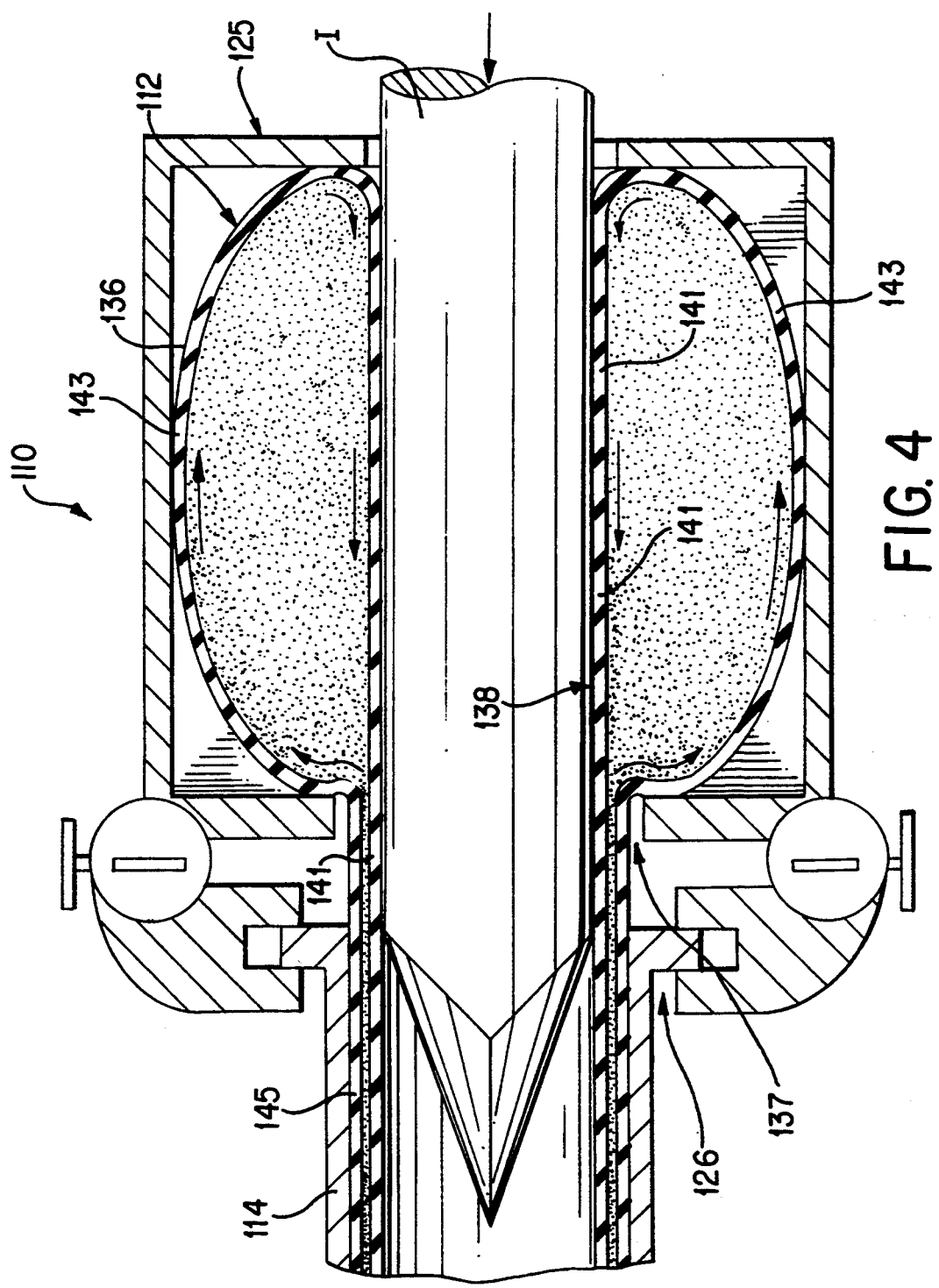
FIG. 4 is an enlarged, broken sectional view of a modification of an endoscopic portal according to the present invention showing the valve assembly therefor.
Figure 5:
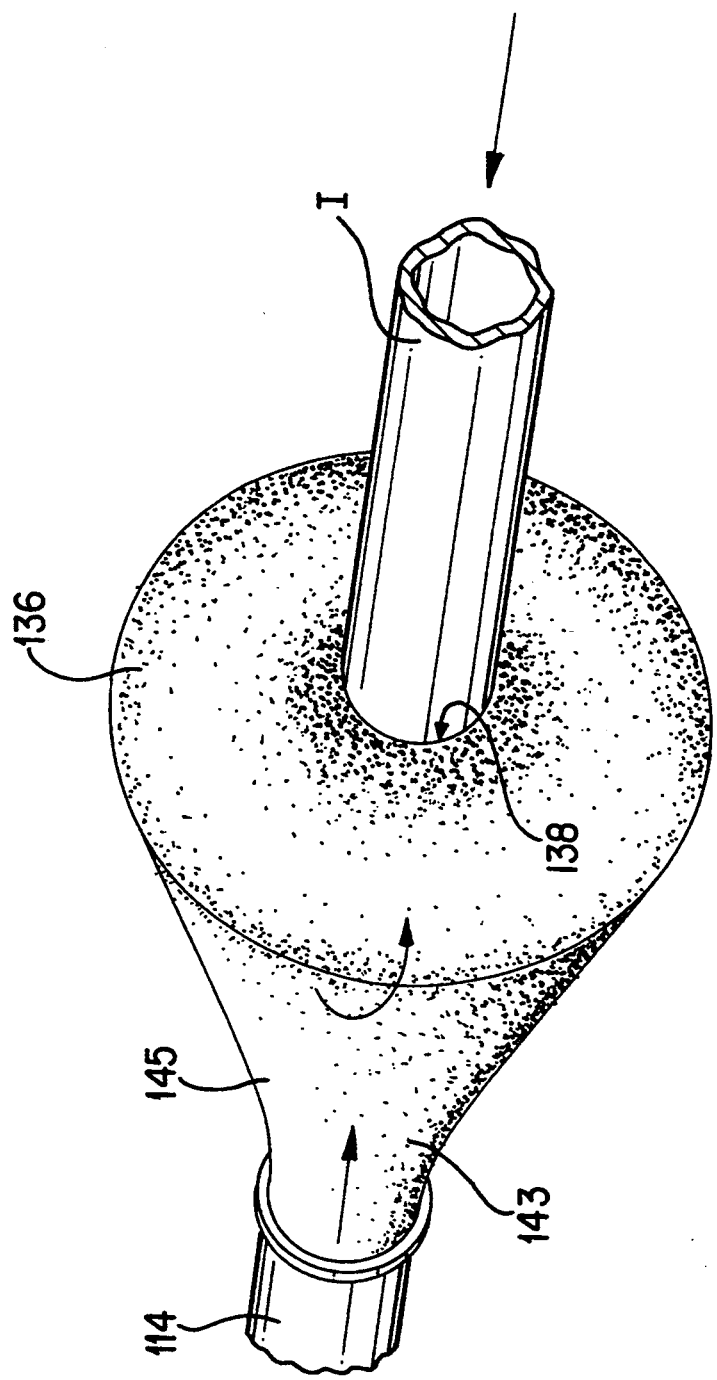
FIG. 5 is a broken perspective view of the valve assembly of FIG. 4 with an instrument extending therethrough.
Figure 6:
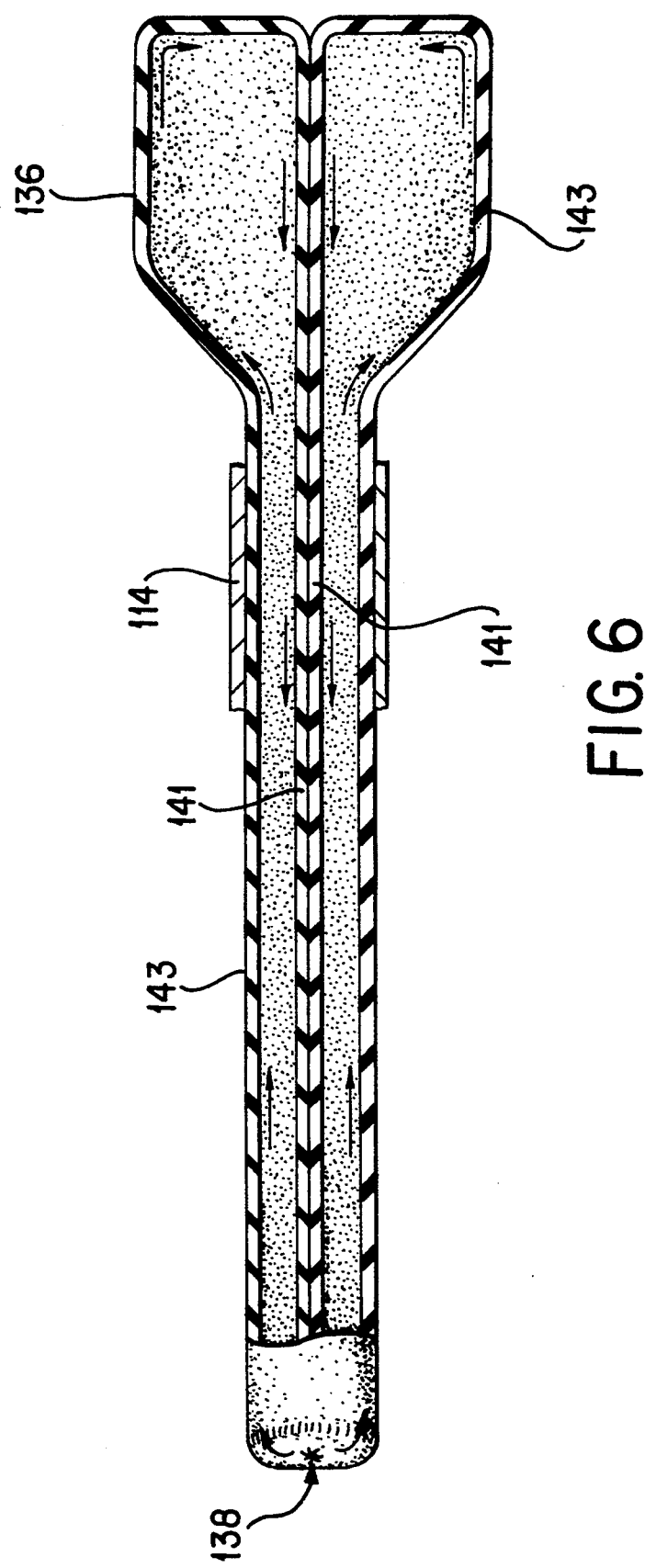
FIG. 6 is a side sectional view of the valve assembly of FIG. 4.

A modification of an endoscopic portal according to the present invention is illustrated at 110 in FIGS. 4–6. Endoscopic portal 110 is similar to endoscopic portal 10 except that the valve assembly 112 for endoscopic portal 110 extends into portal sleeve 114. Valve assembly 112 includes bladder 136 disposed in housing 125, the bladder 136 defining a longitudinal valve passage 138 therethrough. Bladder 136 includes an elongate, distal extension 145 extending through opening 137 and aperture 126 to extend into portal sleeve 114. Extension 145 can be nipple-like in configuration and can extend partially or entirely through the portal sleeve 114 to form a seal with instruments introduced through the portal sleeve. Accordingly, valve passage 138 and walls 141 defining valve passage 138 extend into the portal sleeve 114 to form a seal with instruments or objects along all or part of the length of the portal sleeve 114.

Operation of endoscopic portal 110 is similar to that described for endoscopic portal 10 in that walls 141 defining valve passage 138 are normally closed to form a seal along the length of the valve assembly 112 as shown in FIG. 6 and are opened by an instrument I inserted through the valve passage 138 as shown in FIG. 4. The instrument I is moved forwardly along the valve passage 138 and into sleeve 114 while being sealingly contacted by bladder 136 along valve passage 138. Movement of instrument I in the direction of insertion shown by the arrow in FIG. 4 causes movement of bladder 136 including extension 145 with the instrument. Movement of bladder 136 with instrument I causes the walls 141 to be moved in the direction of insertion and the walls 143 opposite the walls 141 to be moved in a direction opposite the direction of movement of walls 141 as shown by the arrows in FIGS. 5 and 6. With the valve assembly 112 a seal is obtained with instrument I along the length of the portal sleeve 114 for enhanced sealing and support of instrument I.

With the valve assemblies of the present invention, a single valve passage for receiving instruments and objects can be opened to various sizes corresponding to the sizes of instruments and objects passing therethrough in sealing relation with the valve assemblies. By providing the valve passage to be normally closed and to be compressed around instruments passing therethrough, fluid flow through the valve assemblies is prevented prior to insertion of, during insertion of and upon removal of the instruments. Continuous rolling, rotation or inverting movement of the valve assembly bladder in response to movement of instruments along the valve passage permits enhanced gripping of the instruments by the valve assembly while avoiding tearing, catching or snagging for smooth insertion. Movement of the valve assembly bladder with the inserted instruments allows the use of strong compressive or sealing forces without damage to the bladder by the instruments during insertion and withdrawal. The passage of the valve assemblies can be caused to conform to the size and shape of instruments passing therethrough such that more than one instrument can be passed simultaneously through the valve assemblies as well as irregularly shaped instruments and objects. By providing an expandable endoscopic portal, the present invention permits instruments and objects larger than the diameter of the lumen of the portal sleeve to be inserted in and removed from an anatomical cavity.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An endoscopic portal for establishing communication with an anatomical cavity through a wall of the cavity comprising an elongate tubular portal sleeve for insertion through the cavity wall and having a distal end for positioning within the cavity and a proximal end for positioning externally of the cavity; and a valve assembly disposed adjacent said portal sleeve proximal end and including a bladder having a valve passage therethrough, said valve passage being normally closed and being variably opened by an instrument inserted in said portal sleeve through said valve passage, said bladder having walls forming said valve passage and movable by contact with the instrument to move along with the instrument as the instrument passes through said valve assembly.

2. An endoscopic portal as recited in claim 1 wherein said bladder is filled with a compressible material causing said valve passage to be compressed around the instrument in sealing contact therewith and allowing said valve passage to be opened to various sizes to receive instruments of various sizes in sealing engagement therewith.

3. An endoscopic portal as recited in claim 1 and further including a housing mounting said proximal end of said portal sleeve and wherein longitudinal movement of said bladder is confined within said housing.

4. An endoscopic portal for establishing communication with an anatomical cavity through a wall of the cavity comprising an elongate portal sleeve having a lumen therein for being inserted through the cavity wall to establish communication with the cavity; and a valve assembly coupled with said lumen in said portal sleeve and including a bladder having walls forming a valve passage allowing passage therethrough by an instrument to be introduced in the cavity, said bladder being filled with a material allowing said valve passage to be normally closed and to conform to the size of the instrument to sealingly contact instrument to prevent passage of fluid thereby, said bladder walls forming said valve passage being inverted by contact with the instrument as the instrument moves through said valve assembly.

5. An endoscopic portal as recited in claim 4 and further including a housing mounting said portal sleeve and wherein said bladder is disposed in said housing, said housing having walls confining said bladder against longitudinal displacement.

6. An endoscopic portal as recited in claim 5 wherein said housing has a rear wall and an internal shoulder spaced distally from said rear wall and said bladder is disposed between said rear wall and said shoulder to prevent longitudinal displacement of said bladder.

7. An endoscopic portal as recited in claim 5 wherein said bladder is deformable to cause said valve passage to conform to instruments of various sizes in said valve passage.

8. A method of introducing an instrument through a wall of an anatomical cavity including the steps of inserting the instrument in a valve passage through a bladder, the valve passage being formed by walls of the bladder to have a normally closed position;

expanding the valve passage to accommodate the instrument while maintaining the valve passage in sealing contact with the instrument; and moving the walls of the bladder forming the valve passage by contact with the instrument and in response to movement of the instrument through the valve passage.

9. A method of inserting an instrument through an endoscopic portal as recited in claim 8 wherein said step of moving the bladder includes inverting the bladder.

* * * * *